United States Patent [19]

Goda et al.

[11] Patent Number: 5,221,749

[45] Date of Patent: Jun. 22, 1993

[54] PRODUCTION OF DIBENZOXAZOLYLTHIOPHENES

[75] Inventors: Hiroshi Goda; Nario Kimura; Satoshi Kimura; Naohiro Yoshikawa; Masaki Teramoto; Yoshihide Masuda; Yuuji Matuzaki, all of Hyogo, Japan

[73] Assignee: Sumitomo Seika Chemicals Co., Ltd., Hyogo, Japan

[21] Appl. No.: 753,088

[22] Filed: Aug. 30, 1991

Related U.S. Application Data

[62] Division of Ser. No. 492,072, Mar. 12, 1990, Pat. No. 5,093,504.

Foreign Application Priority Data

Mar. 13, 1989 [JP] Japan .................................. 1-61185
Mar. 13, 1989 [JP] Japan .................................. 1-61186
Jul. 19, 1989 [JP] Japan .................................. 1-188546

[51] Int. Cl.$^5$ .......................................... C07D 263/62
[52] U.S. Cl. .................................................... 548/220
[58] Field of Search .......................................... 548/220

[56] References Cited

U.S. PATENT DOCUMENTS 3,255,199 6/1966 Maeder et al. ................ 548/220
5,071,993 12/1991 Leppard ............................. 548/220

FOREIGN PATENT DOCUMENTS 879610 10/1961 United Kingdom ................ 548/220
990466 4/1965 United Kingdom ................ 548/220

OTHER PUBLICATIONS

Kossmehl et al., "Liquid Crystalline Compounds in the Thiophene Series", *Z. Naturforsch*, 38b, 1669-1677, 1983.
Chem. Abstracts, Ogata, vol. 82, 112371w, (1975).
Chem. Abstracts, Kossmehl, vol. 101, 23251a, (1984).
Chem. Abstracts, Torikov, vol. 87, 5747e, (1977).

*Primary Examiner*—Donald G. Daus
*Attorney, Agent, or Firm*—Wegner, Cantor, Mueller & Player

[57] ABSTRACT

There is disclosed a method of producing a thiophene-2,5-dicarboxylic acid diester represented by the formula

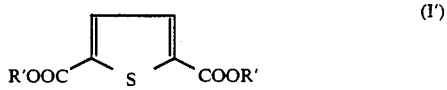
(I')

wherein R' represents an alkyl of 1-8 carbons, a phenyl, a substituted phenyl or benzyl, which comprises:
halogenating a tetrahydrothiophene-2,5-dicarboxylic acid diester represented by the formula

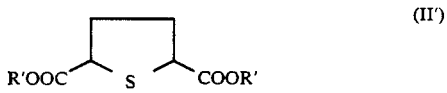
(II')

wherein R' is the same as before, with a halogenating agent selected from the group consisting of halogens and sulfuryl halides in an amount of 2-4 moles per mole of the tetrahydrothiophene-2,5-dicarboxylic acid diester; and then
dehydrohalogenating the resultant halogenated tetrahydrothiophene-2,5-dicarboxylic acid diester in the presence of an alcohol, a base, a metal or a metal ion.

There is also disclosed a method of producing tetrahydrothiophene-2,5-dicarboxylic acid diester and dibenzoxazolyl thiophenes. Some of the thiophene-2,5-dicarboxylic acid diesters and tetrahydrothiophene-2,5-dicarboxylic acid diesters are novel.

5 Claims, No Drawings

PRODUCTION OF DIBENZOXAZOLYLTHIOPHENES

This application is a divisional of Ser. No. 07/492,072, filed Mar. 12, 1990, now U.S. Pat. No. 5,093,504 issued Mar. 3, 1992.

This invention relates to novel thiophene-2,5-dicarboxylic acid diesters and tetrahydrothiophene-2,5-dicarboxylic acid diesters, methods of producing the same, and further to methods of producing dibenzoxazolyl thiophenes.

Thiophene-2,5-dicarboxylic acid diesters are useful intermediates for production of a number of medical and agricultural chemicals. As a further industrial application, hydrolysis of thiophene-2,5-dicarboxylic acid diesters provides thiophene-2,5-dicarboxylic acid which has also wide use.

It is already known, as described in Czechoslovakian Patent No. 137,032, that tetrahydrothiophene-2,5-dicarboxylic acid dimethyl ester is chlorinated to provide 3,4-dichlorotetrahydrothiophene-2,5-dicarboxylic acid dimethyl ester and then the dichlorinated thiophene derivative is thermally decomposed (dehydrochlorinated) to provide thiophene-2,5-dicarboxylic acid dimethyl ester. It is further set forth in the Czechoslovakian Patent No. 137,032 that there are obtained by the method thiophene-2,5-dicarboxylic acid diesters wherein the alkyls are either linear or branched and of 1-8 carbons.

However, the production of the dimethyl ester only is actually disclosed therein, and further, the method is found unsatisfactory in that it provides the dimethyl ester rather in a small yield, and the dimethyl ester is obtained in rather low purity. It is likely that this disadvantage of the method is derived from undesired ester group cleavage side reactions by chlorine in the chlorination of tetrahydrothiophene-2,5-dicarboxylic acid dimethyl ester or undesired tar formation reaction in the thermal decomposition of 3,4-dichlorotetrahydrothiophene-2,5-dicarboxylic acid dimethyl ester.

In turn, there are also already known a number of methods of producing tetrahydrothiophene-2,5-dicarboxylic acid diesters which are not only useful as a starting material for the production of the thiophene-2,5-dicarboxylic acid diesters, but also useful as intermediates for the production of various medicinals and chemicals.

For instance, a method is known in which diethyl α,α'-dibromoadipate is reacted with sodium sulfide in ethanol, to provide tetrahydrothiophene-2,5-dicarboxylic acid diethyl ester, as described in Polymer J., 7(1), 72-78 (1975). A further method is also known wherein the above reaction is carried out in an aqueous acetone in place of ethanol, as described in the Czechoslovakian Patent No. 137,032. However, these methods are found still unsatisfactory from the standpoint of industrial production of the compounds. For instance, the yield of tetrahydrothiophene-2,5-dicarboxylic acid diethyl ester is 33% in the former method. This small yield results from the reaction of sodium sulfide with the ester group of the diethyl α,α'-dibromoadipate to cause hydrolysis of the ester group. This tendency is remarkable in particular when the diesters are lower alkyl esters such as methyl or ethyl esters.

Dibenzoxazolyl thiophenes are useful as fluorescent brightening agents for synthetic resins. Such compounds have been heretofore produced by the reaction of thiophene-2,5-dicarboxylic acid with aminophenols as described in Japanese Patent Laid-open No. 56-92278, or by the reaction of thiophene-2,5-dicarboxylic acid dichloride with aminophenols as described in French Patent No. 1,550,280. The thiophene-2,5-dicarboxylic acid is obtained by hydrolysis of thiophene-2,5-dicarboxylic acid diesters, and the dichloride is obtained by chlorination of thiophene-2,5-dicarboxylic acid. No method has been known which provides a dibenzoxazolyl thiophene in a single step using a thiophene-2,5-dicarboxylic acid diester.

It is, therefore, an object of the invention to provide a novel and industrially advantageous method of producing thiophene-2,5-dicarboxylic acid diesters and tetrahydrothiophene-2,5-dicarboxylic acid diesters.

It is a further object of the invention to provide a novel thiophene-2,5-dicarboxylic acid diester which is produced by the method of the invention.

It is still another object of the invention to provide a novel tetrahydrothiophene-2,5-dicarboxylic acid diester which is produced by the method of the invention.

It is also an object of the invention to provide a method of producing in a single step a dibenzoxazolyl thiophene using a thiophene-2,5-dicarboxylic acid diester as a starting material.

In accordance with the invention, there is provided a method of producing a thiophene-2,5-dicarboxylic acid diester represented by the formula

(I')

wherein R' represents an alkyl of 1-8 carbons, a phenyl, a substituted phenyl or benzyl, which comprises:

halogenating a tetrahydrothiophene-2,5-dicarboxylic acid diester represented by the formula

(II')

wherein R' is the same as before, with a halogenating agent selected from the group consisting of halogens and sulfuryl halides in an amount of 2-4 moles per mole of the tetrahydrothiophene-2,5-dicarboxylic acid diester; and then dehydrohalogenating the resultant halogenated tetrahydrothiophene-2,5-dicarboxylic acid diester in the presence of an alcohol or a base.

In the formulae above and hereinafter, the substituted phenyl includes, for example, mono- or polyalkylated phenyls such as tolyl, ethylphenyl or xylyl, halogenated phenyls such as chlorophenyl, bromophenyl or dichlorophenyl, and alkoxyphenyls such as methoxyphenyl or ethoxyphenyl.

In the halogenation of tetrahydrothiophene-2,5-dicarboxylic acid diesters, there are used, as a halogenating agent, a halogen or a sulfuryl halide, preferably chlorine, bromine, sulfuryl chloride or sulfuryl bromide. These halogenating agents are used in an amount of 2-4 moles, preferably of 2-3 moles, per mole of the tetrahydrothiophene-2,5-dicarboxylic acid diesters used.

It is reasonably assumed that 3,4-dihalotetrahydrothiophene-2,5-dicarboxylic acid diesters, as represented by the formula below, are produced as main reaction products by the halogenation, taking the before mentioned description of the Czechoslovakian Patent No. 137,032 into consideration, possibly together with a minor amount of reaction products otherwise halogenated. Thus, the reaction steps are as follows.

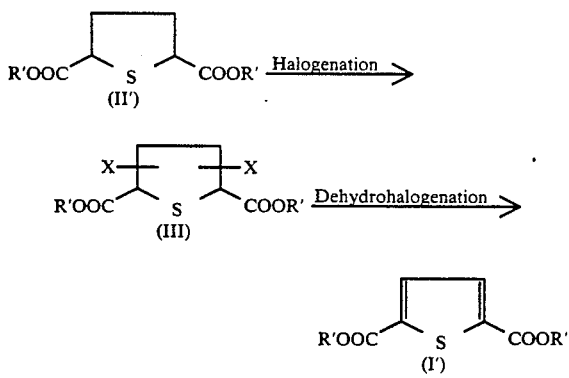

The use of the halogenating agent in an amount of less than 2 moles per mole of tetrahydrothiophene-2,5-dicarboxylic acid diesters provides the desired dichlorinated products only in small yields, whereas with the use of the agent in an amount of more than 4 moles, there take place undesirable side reactions to decrease the yield of the desired 3,4-dihalotetrahydrothiophene-2,5-dicarboxylic acid diesters.

The halogenation of tetrahydrothiophene-2,5-dicarboxylic acid diesters may be carried out either in the presence or in the absence of solvents. The solvent usable may be aromatic hydrocarbons such as benzene, xylene or toluene, halogenated aromatic hydrocarbons such as chlorobenzene, dichlorobenzene or trichlorobenzene, aliphatic hydrocarbons such as n-hexane or n-heptane, alicyclic hydrocarbons such as cyclohexane, or halogenated aliphatic hydrocarbons such as chloroform, dichloroethane or carbon tetrachloride.

The halogenation of tetrahydrothiophene-2,5-dicarboxylic acid diesters may be carried out usually at temperatures ranging from −20° C. to 40° C.,preferably from −15° C. to 30° C. When the reaction temperature is more than 40° C., the yield of the desired products is very small on account of side reactions, whereas no advantage is found in carrying out the reaction at temperatures less than −20° C.

It is necessary to take care of reaction temperature and addition rate of a halogenating agent when tetrahydrothiophene-2,5-dicarboxylic acid dimethyl or diethyl esters are halogenated in order to reduce such undesired side reactions as before mentioned. However, the halogenation of diesters in which the alkyl has 3–8 carbon esters, or of phenyl, substituted phenyl or benzyl esters is little accompanied by such undesired side reactions, so that the desired 3,4-dihalotetrahydrothiophene-2,5-dicarboxylic acid diesters are obtained in high yields.

There is no need of separating the resultant 3,4-dihalotetrahydrothiophene-2,5-dicarboxylic acid diesters, but they are subjected as they are to the subsequent dehydrohalogenation. That is, the halogenation of the tetrahydrothiophene-2,5-dicarboxylic acid diesters and the subsequent dehydrohalogenation is carried out in a so-called one-pot reaction manner.

The dehydrohalogenation of the 3,4-dihalotetrahydrothiophene-2,5-dicarboxylic acid diesters is carried out in the presence of an alcohol or a base in accordance with the invention to provide thiophene-2,5-dicarboxylic acid diesters in higher yields under milder reaction conditions than in the method of the Czechoslovakian Patent No. 137,032. In a most preferred embodiment of the invention, the dehydrohalogenation is carried out in the presence of an alcohol which has the same alkyl as that of the diester which is to be dehydrohalogenated.

It is assumed that the dehydrohalogenation of the 3,4-dihalotetrahydrothiophene-2,5-dicarboxylic acid diesters proceeds by way of a dialkoxytetrahydrothiophene-2,5-dicarboxylicacid diesters represented by the formula

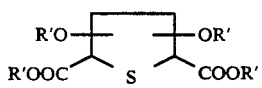

as an intermediate, so that the use of an alcohol provides the desired thiophenedicarboxylic acid diesters in higher yields under milder reaction conditions. Further, when such an alcohol is used which has the same alkyl as that of the desired diesters, there is produced no thiophene-2,5-dicarboxylic acid diesters which have alkyls different from the starting diesters by ester exchange reactions between the diesters and the alcohol used, so that the desired thiophene-2,5-dicarboxylic acid diesters are obtained in higher purity. By way of example, when thiophene-2,5-dicarboxylic acid diisopropyl ester is to be produced, 3,4-dichlorotetrahydrothiophene-2,5-dicarboxylic acid diisopropyl ester is dehydrohalogenated in the presence of isopropyl alcohol.

The amount of an alcohol used in the dehydrohalogenation is usually in the range of 0.2–20 moles, preferably of 2–12 moles, per mole of the starting tetrahydrothiophene-2,5-dicarboxylic acid diesters used. The reaction temperature is usually in the range of 50°–150° C., preferably of 60°–100° C. When the reaction temperature is more than 150° C., there take place undesirable side reactions to decrease the yield of the thiophene-2,5-dicarboxylic acid diesters, while when the reaction temperature is less than 50° C., the reaction proceeds too slowly.

The dehydrohalogenation of 3,4-dihalotetrahydrothiophene-2,5-dicarboxylic acid diesters may be carried out in the presence of a base in place of an alcohol. The base usable includes, for example, alkali metal hydroxides such as sodium hydroxide or potassium hydroxide, amines such as trimethyl amine, triethyl amine or pyridine, alkali metal alcoholates such as sodium methoxide, sodium t-butoxide or potassium t-butoxide. The amount of the base used is not specifically determined since it may depend upon the individual base used. However, the base is used usually in an amount of 2–15 moles, preferably of 2–8 moles, per mole of the starting tetrahydrothiophene-2,5-dicarboxylic acid diesters used.

The reaction is usually carried out at temperatures of 30°–100° C., preferably of 50°–90° C. When the reaction is carried out at temperatures of more than 100° C., the yield of thiophene-2,5-dicarboxylic acid diesters decreases on account of undesired side reactions, whereas when the reaction is carried out at temperatures of less than 30° C., the reaction proceeds too slowly.

The dehydrohalogenation of 3,4-dihalotetrahydrothiophene-2,5-dicarboxylic acid diesters may be carried out either in the presence or in the absence of solvents. When a solvent is used, the same solvent as used in the halogenation of tetrahydrothiophene-2,5-dicarboxylic acid diesters is preferably used.

After the reaction, the resultant thiophene-2,5-dicarboxylic acid diesters may be recovered in any conventional manner such as crystallization or distillation under reduced pressures. When the reaction mixture is treated with water, the resultant thiophene-2,5-dicarboxylic acid diesters are hydrolyzed to provide thiophene-2,5-dicarboxylic acid.

Among the thiophene-2,5-dicarboxylic acid diesters produced by the method of the invention, the methyl and ethyl esters are solid at room temperatures, whereas the branched alkyl esters of 3-8 carbons are liquid at room temperatures. The branched alkyl esters of 3-8 carbons are further different in reactivity in various reactions from the dimethyl or diethyl ester. For instance, the branched alkyl esters provide acid amides in higher yields under milder conditions. Further, the branched alkyl esters provide dibenzoxazolyl thiophenes in higher yields under milder reaction conditions by the reaction with aminophenols than the dimethyl or diethyl esters.

In accordance with the invention, there is provided a further method of producing a thiophene-2,5-dicarboxylic acid diester represented by the formula

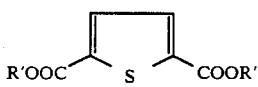

wherein R' represents an alkyl of 1-8 carbons, a phenyl, a substituted phenyl or benzyl, which comprises:

halogenating a tetrahydrothiophene-2,5-dicarboxylic acid diester represented by the formula

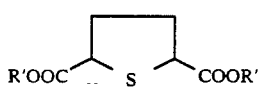

wherein R' is the same as before, with a halogenating agent selected from the group consisting of halogens and sulfuryl halides in an amount of 2-4 moles per mole of the tetrahydrothiophene-2,5-dicarboxylic acid diester; and then dehydrohalogenating the resultant halogenated tetrahydrothiophene-2,5-dicarboxylic acid diester in the presence of a metal selected from the group consisting of Cu, Fe, Zn and Sn, or an ion thereof.

The halogenation stage is the same as before, so that no further description is made herein.

The metal ion used in the dehydrohalogenation stage in this method includes, for example, Cu(I) ion, Cu(II) ion, Fe(II) ion, Fe(III) ion, Zn(II) ion, Sn(II) ion and Sn(IV) ion. These ions are presented usually as halides such as chlorides, bromides or iodides, sulfates or nitrates, and therefore, there may be mentioned as such salts as, for example, cuprous chloride; cupric chloride, cupric sulfate, ferric chloride, zinc chloride or stannous chloride. The halides mentioned above are all chlorides, however, bromides and iodides may be used as well.

In the dehydrohalogenation of halogenized tetrahydrothiophene-2,5-dicarboxylic acid diester in accordance with this second method, the metal or metal ions are used usually in an amount of 0.001-0.1 mole, preferably of 0.005-0.05 moles, per mole of 3,4-dihalotetrahydrothiophene-2,5-dicarboxylic acid diester.

The reaction is carried out usually at temperatures of 70°-130° C., preferably of 80°-120° C. either in the presence or in the absence of solvents. When a solvent is used, the same solvent as used in the halogenation of tetrahydrothiophene-2,5-dicarboxylic acid diesters is preferably used.

As above set forth, there are obtained thiophene-2,5-dicarboxylic acid diesters in simpler operations and in higher yields, such as thiophene-2,5-dicarboxylic acid dimethyl ester, diethyl ester, di-n-propyl ester, diisopropyl ester, di-n-butyl ester, di-n-octyl ester, diphenyl ester, ditolyl ester, di(chlorophenyl) ester or dibenzyl ester.

As an important aspect of the invention, there are obtained novel thiophene-2,5-dicarboxylic acid diesters by making use of the above mentioned method of the invention. Thus, in accordance with the invention, there is provided a novel thiophene-2,5-dicarboxylic acid diester which is represented by the formula

wherein R represents a branched alkyl of 3-8 carbons, a substituted phenyl or benzyl.

The novel thiophene-2,5-dicarboxylic acid diesters of the invention include thiophene-2,5-dicarboxylic acid diisopropyl ester, thiophene-2,5-dicarboxylic acid diisobutyl ester, thiophene-2,5-dicarboxylic acid di-sec-butyl ester, thiophene-2,5-dicarboxylic acid di-tert-butyl ester, thiophene-2,5-dicarboxylic acid di-sec-hexyl ester, thiophene-2,5-dicarboxylic acid di-tert-amyl ester, thiophene-2,5-dicarboxylic acid di-m-tolyl ester, thiophene-2,5-dicarboxylic acid di-p-chlorophenyl ester and thiophene-2,5-dicarboxylic acid dibenzyl ester.

In accordance with the invention, there is further provided a method of producing a tetrahydrothiophene-2,5-dicarboxylic acid diester represented by the formula

wherein R' represents an alkyl of 1-8 carbons phenyl, a substituted phenyl or benzyl, which comprises:

reacting an α,α'-dihaloadipic acid diester represented by the formula

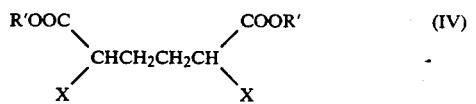

wherein R' is the same as before, and X represents a halogen, preferably chlorine or bromine, with an inorganic sulfide in a two phase solvent composed of a water immiscible organic solvent and water.

The α,α'-dihaloadipic acid diester is readily obtained by halogenating adipic acid with, for example, thionyl chloride, to adipic acid dichloride, further halogenating the dichloride, and then esterification, as described in Org. Syn. Coll. Vol. III, p. 623. The α,α'-dihaloadipic acid diester usable includes, for example, dimethyl α,α'-dichloroadipate, diethyl α,α'-dibromoadipate, diisopropyl α,α'-dichloroadipate, di-sec-butyl α,α'-dichloroadipate, di-tert-butyl α,α'-dibromoadipate, di-n-octyl α,α'-dichloroadipate, di-m-tolyl α,α'-dichloroadipate and dibenzyl α,α'-dichloroadipate.

There may be used, as an inorganic sulfide, for example, an alkali metal sulfide such as sodium sulfide or potassium sulfide, ammonium sulfide, sodium hydrogen sulfide or potassium hydrogen sulfide, with sodium sulfide or potassium sulfide most preferred. The inorganic sulfide is used in an amount of 1–4 moles, preferably of 1–3 moles, per mole of the α,α'-dihaloadipic acid diester used. When the amount of the inorganic sulfide used is too small, there results a small yield of desired tetrahydrothiophene-2,5-dicarboxylic acid diesters, whereas when the amount is too large, there take place undesirable side reactions to reduce the yield of tetrahydrothiophene-2,5-dicarboxylic acid diesters.

The method is featured in the use of a two phase solvent composed of a water immiscible organic solvent and water. As the water immiscible organic solvent may be preferably used an aromatic hydrocarbon such as benzene, toluene or xylene, a halogenated aromatic hydrocarbon such as chlorobenzene, dichlorobenzenes or trichlorobenzenes, or a halogenated aliphatic hydrocarbon such as chloroform, dichloroethane or carbon tetrachloride, or a mixture of two or more of these, with toluene, xylene, chlorobenzene or chloroform, or a mixture of two or more of these being most preferred.

It is necessary that the two phase solvent contains water in an amount sufficient to dissolve therein the by-produced inorganic salts. Thus, the two phase solvent contains water in an amount of 10-100 moles per mole of the α,α'-dihaloadipic acid diester used. On the other hand, it is further necessary that the two phase solvent contains a water immiscible organic solvent in an amount sufficient to dissolve therein the starting α,α'-dihaloadipic acid diester used. It is preferred that the two phase solvent contains the water immiscible organic solvent in an amount of 0.1-10 parts by volume per part by volume of water. When the amount of water is too small, the reaction does not proceed smoothly on account of salts deposited, while when the amount of water is too large, volume efficiency of the reaction is undesirably reduced.

It is not yet clear why the undesirable side reactions are suppressed and tetrahydrothiophene-2,5-dicarboxylic acid diesters are obtained in a much improved yield, however, it is likely that inorganic salts produced in an organic layer wherein a tetrahydrothiophene ring is formed is successively transferred into a water layer so that the reaction proceeds smoothly without side reactions. Further, it is surprising that when a dialkyl ester wherein the alkyl has not less than three carbons, a diphenyl ester, a substituted diphenyl ester or a dibenzyl ester of α,α'-dihaloadipic acid diester is used as a starting material, there take place substantially no side reactions to provide the desired tetrahydrothiophene-2,5-dicarboxylic acid diesters substantially in a quantitative amount.

After the reaction, the organic layer is separated from the aqueous layer, and the organic layer is washed with water, dried and distilled under reduced pressures to remove the solvent. Then, the concentrate is distilled under reduced pressures, to provide tetrahydrothiophene-2,5-dicarboxylic acid diesters. Thus, in accordance with the method of the invention, tetrahydrothiophene-2,5-dicarboxylic acid diesters are obtained in a simple manner. There is no need of filtration of the reaction mixture to remove the inorganic salts from the reaction mixture.

It may be preferred that the reaction is carried out in the presence of a phase transfer catalyst. The phase transfer catalyst usable is not specifically limited, but it may be exemplified by a quaternary ammonium salt such as lauryltrimethylammonium halide or alkyldimethylbenzyl ammonium halide (banzalkonium halide), or a phosphorous compound such as hexadecyltributylphosphonium halide. The quaternary ammonium salt, in particular, a benzalkonium halide represented by

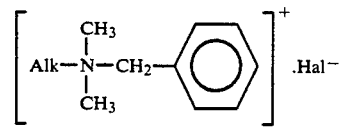

wherein Alk is an alkyl of 12–18 carbons and Hal is a halogen is most preferred since the reaction completes within a short period of time in the presence of such a phase transfer catalyst. The phase transfer catalyst is used usually in an amount of up to 5% by weight based on the α,α'-dihaloadipic acid diester used.

The reaction is carried out at temperatures usually of 10°–100° C., preferably of 20°–60° C. When the reaction temperature is more than 100° C., there take place undesirable side reactions, while when the reaction temperature is less than 10° C., the reaction proceeds too slowly.

After the reaction, the resultant tetrahydrothiophene-2,5-dicarboxylic acid diesters may be recovered and purified, for example, by distillation under reduced pressures, but they may be used as they are in the subsequent reactions.

The reaction as above set forth presents a number of novel tetrahydrothiophene-2,5-dicarboxylic acid diesters. Thus, in accordance with the invention, there is provided a novel tetrahydrothiophene-2,5-dicarboxylic acid diester represented by the formula

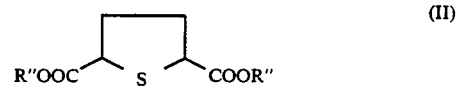

(II)

wherein R" represents an alkyl of 3–8 carbons, phenyl, a substituted phenyl or benzyl.

There may be mentioned, as such a novel tetrahydrothiophene-2,5-dicarboxylic acid diesters, for example, tetrahydrothiophene-2,5-dicarboxylic acid diisopropyl ester, tetrahydrothiophene-2,5-dicarboxylic acid di-n-propyl ester, tetrahydrothiophene-2,5-dicarboxylic acid di-n-butyl ester, tetrahydrothiophene-2,5-dicarboxylic acid diisobutyl ester, tetrahydrothiophene-2,5-dicarboxylic acid di-sec-butyl ester, tetrahydrothiophene-2,5-dicarboxylic acid di-tert-butyl ester, tetrahydrothiophene-2,5-dicarboxylic acid diisoamyl ester, tetrahydrothiophene-2,5-dicarboxylic acid di-n-octyl ester, tetrahydrothiophene-2,5-dicarboxylic acid diphenyl ester, tetrahydrothiophene-2,5-dicarboxylic acid di-m-tolyl ester or tetrahydrothiophene-2,5-dicarboxylic acid dibenzyl ester.

By making use of the novel compounds and methods of the invention described herein, a thiophene-2,5-dicarboxylic acid which is an important intermediate in the production of a number of chemicals may be produced as follows.

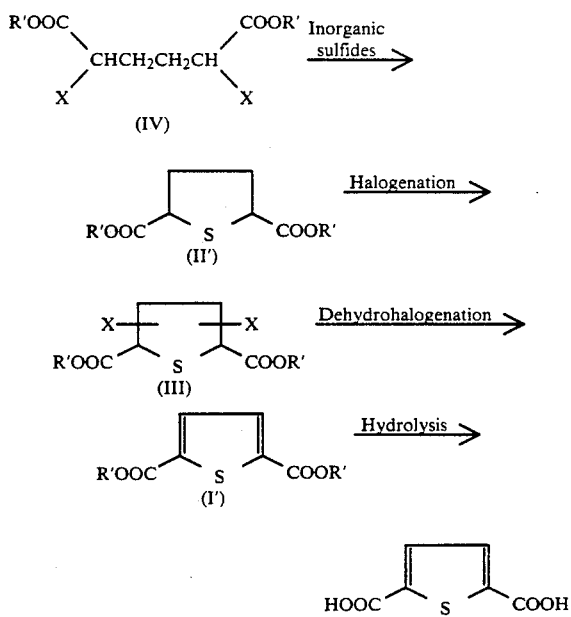

The thiophene-2,5-dicarboxylic acid diester represented by the formula (I') may be hydrolyzed with an alkali or an acid catalyst, as in the conventional hydrolysis reactions, to readily provide thiophene-2,5-dicarboxylic acid.

The compounds represented by the formula (II), (II'), (III) and (IV) as described above contain dl- and meso-isomers, and herein the specification, the compounds represented by the formula (II), (II'), (III) and (IV) are a mixture of the dl- and meso-isomers, respectively.

As a further aspect of the invention, there is provided a method of producing a dibenzoxazolyl thiophene represented by the formula

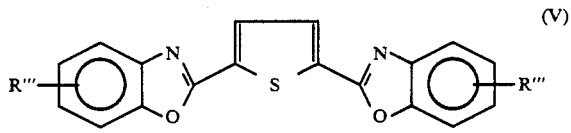

wherein R''' represents a hydrogen, an alkyl of 1-8 carbons, a cycloalkyl, a phenyl, a substituted phenyl or a benzyl, which comprises:

reacting a thiophene-2,5-dicarboxylic acid diester represented by the formula

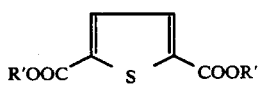

wherein R' represents an alkyl of 1-8 carbons, a phenyl, a substituted phenyl or a benzyl, with an aminophenol represented by the formula

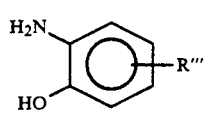

wherein R''' is the same as before, in the presence of an acid catalyst.

The thiophene-2,5-dicarboxylic acid diester usable includes those mentioned hereinbefore, such as thiophene-2,5-dicarboxylic acid dimethyl ester, thiophene-2,5-dicarboxylic acid diethyl ester, thiophene-2,5-dicarboxylic acid di-n-propyl ester, thiophene-2,5-dicarboxylic acid diisopropyl ester, thiophene-2,5-dicarboxylic acid di-n-butyl ester, thiophene-2,5-dicarboxylic acid di-sec-butyl ester, thiophene-2,5-dicarboxylic acid diisobutyl ester, thiophene-2,5-dicarboxylic acid di-tert-butyl ester, thiophene-2,5-dicarboxylic acid diisoamyl ester, thiophene-2,5-dicarboxylic acid di-sec-amyl ester, thiophene-2,5-dicarboxylic acid di-tert-amyl ester, thiophene-2,5-dicarboxylic acid di-n-octyl ester, thiophene-2,5-dicarboxylic acid diphenyl ester, thiophene-2,5-dicarboxylic acid di-m-tolyl ester or thiophene-2,5-dicarboxylic acid dibenzyl ester. Among these diesters are preferred in particular diisoproyl, diisobutyl, di-sec-butyl, di-tert-butyl, diisoamyl, di-sec-amyl, di-tert-amyl or diphenyl esters since the reaction proceeds very rapidly to provide the desired dibenzoxazolyl thiophene derivatives.

The aminophenol used includes, for instance, 2-aminophenol, 4-methyl-2-aminophenol, 4-ethyl-2-aminophenol, 4-n-propyl-2-aminophenol, 4-isopropyl-2-aminophenol, 4-n-butyl-2-aminophenol, 4-isobutyl-2-aminophenol, 4-sec-butyl-2-aminophenol, 4-tert-butyl-2-aminophenol, 4-n-octyl-2-aminophenol, 4-cyclohexyl-2-aminophenol, 4-phenyl-2-aminophenol and 4-benzyl-2-aminophenol. The aminophenol is used usually in an amount of 1.8-3.0 moles, preferably of 2.0-2.6 moles, per mole of thiophene-2,5-dicarboxylic acid diester used.

The acid catalyst used in the invention includes, for example, boric acid, phosphoric acid, polyphosphoric acid, zinc chloride, ferric chloride and sulfuric acid, among which boric acid is most preferred. The amount of the acid catalyst is usually in the range of 0.05-0.50 moles per mole of thiophene dicarboxylic acid diester.

It is desired that the reaction is carried out under an inert gas atmosphere such as nitrogen to prevent coloration of the dibenzoxazolyl thiophene produced. It is also desired that the reaction is carried out while alcohol and water produced are removed from the reaction mixture by distillation so that the reaction proceeds smoothly.

Accordingly, the reaction is carried out preferably at temperatures of 150°-300° C., most preferably of 180°-270° C. so that the alcohol and water produced during the reaction are removed from the reaction mixture in a moment, thereby to provide the dibenzoxazolyl thiophene in high yields.

The reaction may be effected either in the presence or in the absence of a solvent. When a solvent is used, it is selected so as to permit the adoption of reaction temperature as above mentioned. Therefore, there may be used, as a solvent, for example, such a halogenated aromatic hydrocarbon as dichlorobenzenes or trichlorobenzenes, polyhydric alcohols such as ethylene glycol, glycerine, N,N-dimethylformamide, dimethylsulfoxide or diphenyl ether, depending upon the reaction temperature adopted.

There may be obtained by the method, for instance, 2,5-bis(2-benzoxazolyl)thiophene, 2,5-bis[5-methylbenzoxazolyl-(2')]thiophene, 2,5-bis[5-ethylbenzoxazolyl-(2')]thiophene, 2,5-bis[5-n-propylbenzoxazolyl-(2')]thiophene, 2,5-bis[5-isopropylbenzoxazolyl-(2')]thiophene, 2,5-bis[5-n-butylbenzoxazolyl-(2′)]thiophene, 2,5-bis[5-sec-butylbenzoxazolyl-(2′)]thiophene, 2,5-bis[5-isobutylbenzoxazolyl-(2′)]thiophene, 2,5-bis[5-tert-butylbenzoxazolyl-(2′)]thiophene, 2,5-bis[5-n-octylbenzoxazolyl-(2′)]thiophene, 2,5-bis[5-phenylbenzoxazolyl-(2′)]thiophene or 2,5-bis[5-benzylbenzoxazolyl-(2′)]thiophene.

Now the invention will be described more specifically with reference to examples, however, the invention is not limited to the examples.

SYNTHESIS OF THIOPHENE-2,5-DICARBOXYLIC ACID DIESTERS

EXAMPLE 1

In a 300 ml capacity four necked flask provided with a stirrer, a thermometer, a gas inlet and a cooling tube were placed 28.8 g (0.10 mole) of tetrahydrothiophene-2,5-dicarboxylic acid di-n-butyl ester (prepared in the Example 20 described hereinafter) and 100 ml of chlorobenzene, and then an amount of 14.9 g (0.21 mole) of chlorine was introduced into the mixture at a temperature ranging from −10° C. to −5° C. under stirring over a period of one hour. Thereafter, the mixture was stirred at the temperature for another one hour.

After the reaction, an amount of 80 g (1.08 mole) of n-butanol was added to the reaction mixture, and the mixture was stirred at 80° C. over six hours.

After the completion of dehydrochlorination reaction, n-butanol and chlorobenzene were removed by distillation under reduced pressures, and the residue was further distilled under reduced pressures, to provide 26.5 g of thiophene-2,5-dicarboxylic acid di-n-butyl ester as a colorless liquid. The yield was found to be 93.3% based on tetrahydrothiophene-2,5-dicarboxylic acid di-n-butyl ester.

The purity, boiling point and analytical data of thiophene-2,5-dicarboxylic acid di-n-butyl ester are shown in the Table 2.

EXAMPLES 2–12 AND COMPARATIVE EXAMPLES 1 AND 2

The halogenation and subsequent dehydrochlorination were carried out in the same manner as in the Example 1 using tetrahydrothiophene-2,5-dicarboxylic acid diesters (0.10 mole), solvents (100 ml) and chlorinating agent (0.21 mole) as shown in the Table 1. When the resultant thiophene-2,5-dicarboxylic acid diester was liquid, it was isolated by distillation under reduced pressures, while, if the resultant thiophene-2,5-dicarboxylic acid diester was solid, it was collected by filtration and recrystallized. The results are shown in the Table 1.

For comparison, the dehydrochlorination was carried out in the absence of alcohols, and the results are shown as Comparative Examples 1 and 2 in the Table 1.

The purity, boiling point and analytical data of the thiophene-2,5-dicarboxylic acid diester thus obtained in the Examples 1–11 are shown in the Table 2.

TABLE 1

| Examples | Start Material R'OOC–S–COOR' (0.10 mole) | Solvent (100 ml) | Chlorinating Agent (0.21 mole) | Additive (Alcohol) (mole) | Product R'OOC–S–COOR' | Yield (%) |
|---|---|---|---|---|---|---|
| 1 | R' = n-butyl | chlorobenzene | $Cl_2$ | n-butanol (1.08) | R' = n-butyl | 93.3 |
| 2 | R' = methyl | chlorobenzene | $Cl_2$ | methanol (1.88) | R' = methyl | 78.5 |
| 3 | R' = ethyl | chlorobenzene | $Cl_2$ | ethanol (1.30) | R' = ethyl | 80.4 |
| 4 | R' = isopropyl | chlorobenzene | $Cl_2$ | isopropanol (1.00) | R' = isopropyl | 93.1 |
| 5 | R' = tert-butyl | chlorobenzene | $Cl_2$ | tert-butanol (1.08) | R' = tert-butyl | 82.6 |
| 6 | R' = isobutyl | 1,2,4-trichlorobenzene | $Cl_2$ | isobutanol (0.54) | R' = isobutyl | 94.0 |
| 7 | R' = sec-butyl | 1,2,4-trichlorobenzene | $Cl_2$ | sec-butanol (1.08) | R' = sec-butyl | 95.4 |
| 8 | R' = n-ocytl | chlorobenzene | $Cl_2$ | n-octanol (1.00) | R' = n-octyl | 92.9 |
| 9 | R' = phenyl | chlorobenzene | $Cl_2$ | phenol (0.25) | R' = phenyl | 91.8 |
| 10 | R' = m-tolyl | chlorobenzene | $Cl_2$ | m-cresol (0.25) | R' = m-tolyl | 92.1 |
| 11 | R' = benzyl | chlorobenzene | $SO_2Cl_2$ | benzyl alcohol (0.93) | R' = benzyl | 94.3 |
| 12 | R' = n-butyl | 1,2,4-trichlorobenzene | $Cl_2$ | n-butanol (1.08) | R' = n-butyl | 93.3 |
| Compara. 1 | R' = methyl | chlorobenzene | $Cl_2$ | — | R' = methyl | 59.6 |
| Compara. 2 | R' = m-tolyl | chlorobenzene | $Cl_2$ | — | R' = m-tolyl | 75.3 |

TABLE 2

| Examples | GC-Purity Area % | Appearance | Mp. or Bp. (°C. or °C./mmHg) | Mass m/e | NMR Signal | Elemental Analysis (%) Upper: Observed (Lower: Calculated) | | |
|---|---|---|---|---|---|---|---|---|
| | | | | | | C | H | S |
| 1 | >99 | transparent, colorless liquid | 145–150/3 | 284 | 7.7(s. 2H) 4.3(t. 4H) 1.9–1.2(m. 4H) 1.0(t. 6H) | 58.5 (59.1) | 7.00 (7.09) | 12.0 (11.3) |
| 2 | >99 | white crystal | 149–150 | 200 | 7.75(s. 2H) 3.9(s. 6H) | 48.9 (48.0) | 4.00 (4.03) | 16.8 (16.0) |
| 3 | >99 | white crystal | 51–52 | 228 | 7.75(s. 2H) 1.5–1.2(t. 6H) 4.4–4.0(q. 4H) | 52.5 (52.6) | 5.28 (5.30) | 14.8 (14.0) |
| 4 | >99 | transparent, colorless liquid | 145–150/3 | 256 | 7.8(s. 2H) 5.5–5.0(m. 2H) 1.35(d. 12H) | 55.8 (56.2) | 6.20 (6.29) | 13.0 (12.5) |
| 5 | >99 | transparent, colorless | 145–150/3 | 284 | 7.7(s. 2H) 1.6(m. 18H) | 58.5 (59.1) | 7.04 (7.09) | 12.1 (11.3) |
| 6 | >99 | transparent, colorless liquid | 145–150/3 | 284 | 7.7(s. 2H) 4.0(m. 2H) 2.0–1.2(m. 4H) 0.9(d. 12H) | 59.5 (59.1) | 7.12 (7.09) | 12.1 (11.3) |
| 7 | >99 | transparent, colorless liquid | 160–165/3 | 284 | 7.7(s. 2H) 5.4–4.7(m. 2H) 2.1–1.4(m. 4H) 1.35(d. 6H) 1.0(t. 6H) | 59.0 (59.1) | 7.05 (7.09) | 11.0 (11.3) |
| 8 | >99 | white crystal | 125–126 | 397 | 7.8(s. 2H) 4.8–3.0(m. 4H) 3.0–1.1(m. 24H) 0.9(t. 6H) | 66.9 (66.6) | 9.10 (9.15) | 8.12 (8.08) |
| 9 | >99 | white crystal | 135–136 | 324 | 7.9(s. 2H) 7.8–6.5(m. 10H) | 66.5 (66.7) | 3.70 (3.73) | 9.90 (9.89) |
| 10 | >99 | white crystal | 174–175 | 352 | 7.9(s. 2H) 7.5–6.8(m. 8H) 2.35(s. 6H) | 69.0 (68.2) | 4.50 (4.58) | 9.20 (9.10) |
| 11 | >99 | white crystal | 78–80 | 352 | 7.75(s. 2H) 7.35(s. 10H) 5.3(s. 4H) | 68.5 (68.2) | 4.59 (4.58) | 9.19 (9.10) |

EXAMPLE 13

In a 300 ml capacity four necked flask provided with a stirrer, a thermometer, a gas inlet and a cooling tube were placed 23.2 g (0.10 mole) of tetrahydrothiophene-2,5-dicarboxylic acid diethyl ester (prepared in the Example 28 described hereinafter) and 100 ml of chlorobenzene, and then an amount of 14.9 g (0.21 mole) of chlorine was introduced into the mixture at a temperature ranging from −10° C. to −5° C. under stirring over a period of one hour. Thereafter, the mixture was stirred at the temperature for another one hour.

After the reaction, an amount of 40.4 g (0.40 mole) of triethylamine was added dropwise to the reaction mixture, and the mixture was stirred at 50°–60° C. over two hours.

After the completion of the dehydrochlorination reaction, the reaction mixture was washed with water to remove the resultant triethylamine hydrochloride therefrom, and then the remaining triethylamine and chlorobenzene were removed by distillation under reduced pressures. Then, ethanol was added to the residue, whereupon white crystals precipitated, which were collected by filtration and amounted to 18.4 g.

The yield was found to be 80.7% based on tetrahydrothiophene-2,5-dicarboxylic acid diethyl ester.

EXAMPLE 14

In a 100 ml capacity four necked flask provided with a stirrer, a thermometer, a gas inlet and a cooling tube were placed 26.0 g (0.10 mole) of tetrahydrothiophene-2,5-dicarboxylic acid diisopropyl ester (prepared in the Example 17 described hereinafter), and then an amount of 14.9 g (0.21 mole) of chlorine was introduced into the mixture at a temperature ranging from −10° C. to −5° C. under stirring over a period of one hour. Thereafter the mixture was stirred at the temperature for one hour longer.

After the chlorination reaction, an amount of 5 g of water was added, and then an amount of 16 g (0.40 mole) of solid sodium hydroxide was added gradually, followed by stirring at 50°–60° C. over a period of three hours.

After the completion of the dehydrochlorination reaction, chloroform and water were added to the reaction mixture, the chloroform solution was fully washed with water, and the chloroform solution was concentrated by distilling off chloroform. The residue was distilled under reduced pressures to provide 20.1 g of thiophene-2,5-dicarboxylic acid diisopropyl ester as a colorless and transparent liquid.

The yield was found to be 78.5% based on tetrahydrothiophene-2,5-dicarboxylic acid diisopropyl ester.

SYNTHESIS OF TETRAHYDROTHIOPHENE-2,5-DICARBOXYLIC ACID DIESTERS

EXAMPLE 15

In a 300 ml capacity four necked flask provided with a stirrer, a thermometer, a dropping funnel and a cooling tube were placed 38.8 g (0.10 mole) of α,α'-dibromoadipic acid di-n-propyl ester, 100 ml of chlorobenzene and 0.3 g of benzalkonium chlorides (in which those having an alkyl of 14 carbons amounted to more than 80%) as a phase transfer catalyst.

An aqueous solution of 13.65 g (0.105 mole) of 60% sodium sulfide in 100 ml of water was added dropwise to the above mixture at a temperature of 40°–50° C. over a period of one hour under stirring, and then the mixture was stirred at the temperature for another two hours.

The resultant reaction mixture was separated into a chlorobenzene layer and an aqueous layer. The organic layer was washed with water, dried, and then chlorobenzene was removed therefrom by distillation under reduced pressures. The residue was further distilled under reduced pressures, to provide 22.9 g of tetrahydrothiophene-2,5-dicarboxylic acid di-n-propyl ester in a yield of 88.1% based on α,α'-dibromoadipic acid di-n-propyl ester.

The boiling point and analytical data of tetrahydrothiophene-2,5-dicarboxylic acid di-n-propyl ester are shown in the Table 4.

EXAMPLES 16–28

The reaction was carried out in the same manner as in the Example 15 using α,α'-dihaloadipic acid diesters (0.10 mole), inorganic sulfides (0.105 mole), phase tranfer catalysts (0.3 g) and two phase solvents as shown in the Table 3. When the resultant tetrahydrothiophene-2,5-dicarboxylic acid diester was liquid, it was isolated by distillation under reduced pressures, while if the resultant tetrahydrothiophene-2,5-dicarboxylic acid diester was solid, a water immiscible organic layer was separated from the reaction mixture, the organic solvent was removed by distillation, and the residue was purified in a conventional manner. The results are shown in the Table 3.

The boiling point and analytical data of the tetrahydrothiophene-2,5-dicarboxylic acid diester thus obtained in the Examples 15–25 and 28 are shown in the Table 4.

TABLE 3

| Examples | Start Material R'OOC-X X-COOR' (0.10 mole) | Water Immiscible Solvent (Solvent/Water Volume Ratio) | Inorganic Sulfide (0.105 mole) | Phase Transfer Catalyst[1] (0.3 g) | Product R'OOC-S-COOR' | Yield (%) |
|---|---|---|---|---|---|---|
| 15 | X = Br<br>R' = n-propyl | chlorobenzene (1.0) | 60% sodium sulfide | benzalkonium chloride ($C_{14} > 80\%$) | R' = n-propyl | 88.1 |
| 16 | X = Br<br>R' = methyl | chlorobenzene (1.0) | 60% sodium sulfide | benzalkonium chloride ($C_{14} > 80\%$) | R' = methyl | 81.1 |
| 17 | X = Br<br>R' = isopropyl | chlorobenzene (0.5) | 60% sodium sulfide | benzalkonium chloride ($C_{18} > 80\%$) | R' = isopropyl | 93.5 |
| 18 | X = Br<br>R' = isobutyl | chloroform (0.3) | 60% sodium sulfide | benzalkonium chloride ($C_{18} > 80\%$) | R' = isobutyl | 94.4 |
| 19 | X = Br<br>R' = sec-butyl | chloroform (0.3) | 60% sodium sulfide | hexadecyltributylphosphonium bromide | R' = sec-butyl | 90.5 |
| 20 | X = Br<br>R' = n-butyl | chloroform (0.5) | 60% sodium sulfide | hexadecyltributylphosphonium bromide | R' = n-butyl | 93.3 |
| 21 | X = Br<br>R' = tert-butyl | chloroform (0.5) | 60% potassium sulfide | lauryltrimethylammonium chloride | R' = tert-butyl | 95.3 |
| 22 | X = Br<br>R' = n-octyl | chlorobenzene (3.0) | 60% sodium sulfide | lauryltrimethylammonium chloride | R' = n-octyl | 91.1 |
| 23 | X = Br<br>R' = m-tolyl | chloroform (4.0) | 60% sodium sulfide | benzalkonium chloride ($C_{12} > 80\%$) | R' = m-tolyl | 89.3 |
| 24 | X = Br<br>R' = phenyl | chloroform (6.0) | 60% sodium sulfide | benzalkonium chloride ($C_{14} > 80\%$) | R' = phenyl | 87.2 |
| 25 | X = Br<br>R' = benzyl | chloroform (4.0) | 60% potassium sulfide | benzalkonium chloride ($C_{14} > 80\%$) | R' = benzyl | 93.4 |
| 26 | X = Cl<br>R' = isobutyl | toluene (0.8) | 60% sodium sulfide | hexadecyltributylphosphonium bromide | R' = isobutyl | 92.8 |
| 27 | X = Cl<br>R' = isopropyl | toluene (1.0) | 60% sodium sulfide | hexadecyltributylphosphonium bromide | R' = isopropyl | 91.3 |
| 28 | X = Br<br>R' = ethyl | chlorobenzene (1.0) | 60% sodium sulfide | benzalkonium chloride ($C_{18} > 80\%$) | R' = ethyl | 82.3 |

Note:
[1] When benzalkonium chlorides are used, $C_{14} > 80\%$, for example, means that more than 80% have an alkyl of 14 carbons.

TABLE 4

| Examples | GC-Purity Area % | Appearance | Mp. or Bp. (°C. or °C./mmHg) | Mass m/e | NMR Signal | Elemental Analysis (%) Upper: Observed (Lower: Calculated) C | H | S |
| --- | --- | --- | --- | --- | --- | --- | --- | --- |
| 15 | >99 | transparent, colorless liquid | 143–147/4 | 260 | 4.4–3.4(m. 8H)<br>2.7–2.0(m. 4H)<br>1.9–1.1(m. 8H) | 54.5 (55.4) | 7.81 (7.74) | 12.9 (12.3) |
| 16 | >99 | transparent, colorless liquid | 134–140/5 | 204 | 4.3–3.8(m. 2H)<br>3.7(s. 6H)<br>2.7–2.0(m. 4H) | 46.5 (47.0) | 6.08 (5.92) | 15.2 (15.7) |
| 17 | >99 | transparent, colorless liquid | 145–150/3 | 260 | 5.3–4.7(m. 2H)<br>4.4–3.7(m. 2H)<br>2.8–1.8(m. 4H)<br>1.25(d. 12H) | 56.2 (55.4) | 7.75 (7.74) | 12.8 (12.3) |
| 18 | >99 | transparent, colorless liquid | 170/7 | 288 | 4.3–3.7(m. 2H)<br>3.9(d. 4H)<br>2.8–1.6(m. 6H)<br>0.95(d. 12H) | 58.7 (58.3) | 8.48 (8.39) | 10.5 (11.1) |
| 19 | >99 | transparent, colorless liquid | 160–165/3 | 288 | 5.2–4.5(m. 2H)<br>4.2–3.7(m. 2H)<br>2.8–1.9(m. 4H)<br>1.55(m. 4H)<br>1.2(d. 6H)<br>0.9(t. 6H) | 58.1 (58.3) | 8.27 (8.39) | 12.0 (11.1) |
| 20 | >99 | transparent, colorless liquid | 165/4 | 288 | 4.5–3.7(m. 2H)<br>4.1(t. 4H)<br>2.8–1.9(m. 4H)<br>1.9–1.1(m. 8H)<br>0.95(t. 6H) | 57.8 (58.3) | 8.49 (8.39) | 10.2 (11.1) |
| 21 | >99 | transparent, colorless liquid | 140–145/4 | 288 | 4.0–3.6(s. 2H)<br>2.6–1.8(m. 4H)<br>1.4(s. 18H) | 59.1 (58.3) | 8.45 (8.39) | 10.2 (11.1) |
| 22 | >99 | transparent, colorless liquid | 210–215/2 | 401 | 4.5–3.7(m. 2H)<br>4.0(t. 4H)<br>3.0–1.1(m. 28H)<br>0.9(t. 6H) | 67.0 (66.0) | 10.9 (10.1) | 8.01 (8.00) |
| 23 | >99 | colorless solid | 69–71 | 356 | 7.5–6.7(m. 8H)<br>4.7–4.1(m. 6H)<br>2.5(s. 6H) | 67.8 (67.4) | 5.59 (5.66) | 9.08 (9.00) |
| 24 | >99 | colorless solid | 52–54 | 328 | 7.8–6.5(m. 10H)<br>4.5–4.0(m. 2H)<br>3.0–2.0(m. 4H) | 65.2 (65.8) | 4.95 (4.91) | 9.85 (9.76) |
| 25 | >99 | colorless solid or transparent, colorless liquid | 30–33<br>225–230/4 | 356 | 7.3(s. 10H)<br>5.1(s. 4H)<br>4.2–3.8(m. 2H)<br>2.8–1.9(m. 4H) | 68.0 (67.4) | 5.69 (5.66) | 9.01 (9.00) |
| 28 | >99 | transparent, colorless liquid | 128–130/5 | 232 | 4.5–3.8(m. 6H)<br>2.7–1.9(m. 4H)<br>1.6–1.2(t. 6H) | 51.2 (51.7) | 6.90 (6.94) | 13.9 (13.8) |

SYNTHESIS OF TETRAHYDROTHIOPHENE-2,5-DICARBOXYLIC ACID DIMETHYL ESTER

COMPARATIVE EXAMPLE 3

In a 500 ml capacity four necked flask provided with a stirrer, a thermometer, a dropping funnel and a cooling tube were placed 33.2 g (0.10 mole) of α,α'-dibromoadipic acid dimethyl ester and 100 ml of methanol.

A solution of 13.65 g (0.105 mole) of 60% sodium sulfide in 200 ml of methanol was added dropwise to the above mixture at a temperature of 40°–50° C. over a period of one hour under stirring, and then the mixture was stirred at the temperature for another two hours.

Methanol was removed from the reaction mixture by distillation under reduced pressures, and ethyl acetate and water were added to the residue. The mixture was separated into an ethyl acetate layer and an aqueous layer, and the ethyl acetate layer was washed with water, dried, and then concentrated by distilling off ethyl acetate under reduced pressures. The residue was further distilled under reduced pressures, to provide 11.5 g of tetrahydrothiophene-2,5-dicarboxylic acid dimethyl ester as a transparent liquid in a yield of 56.4% based on dimethyl α,α'-dibromoadipate.

SYNTHESIS OF THIOPHENE-2,5-DICARBOXYLIC ACID DIESTERS

EXAMPLE 29

In a 300 ml capacity four necked flask provided with a stirrer, a thermometer, a gas inlet and a cooling tube were placed 28.8 g (0.10 mole) of tetrahydrothiophene-2,5-dicarboxylic acid di-n-butyl ester and 100 ml of cyclohexane, and then an amount of 14.9 g (0.21 mole) of chlorine was introduced into the mixture at a temperature ranging from −10° C. to −5° C. under stirring over a period of one hour. Thereafter, the mixture was stirred at the temperature for one other hour.

After the chlorination reaction, an amount of 0.318 g (0.0050 mole) of copper powder was added to the reaction mixture. The mixture was then stirred at 105° C. over eight hours while the cyclohexane was removed therefrom by distillation, thereby to effect dehydrochlorination.

After the completion of dehydrochlorination reaction, the residue was distilled under reduced pressures, to provide 27.3 g of thiophene-2,5-dicarboxylic acid di-n-butyl ester as a transparent liquid having a gas chromatographic purity of more than 99.0%. The yield was found to be 96.0% based on tetrahydrothiophene-2,5-dicarboxylic acid di-n-butyl ester.

EXAMPLES 30-40

The halogenation and subsequent dehydrochlorination were carried out in the same manner as in the Example 29 using tetrahydrothiophene-2,5-dicarboxylic acid diesters (0.10 mole), solvents (100 ml), chlorinating agents (0.21 mole) and metals or metal ions as shown in the Table 5.

When the resultant thiophene-2,5-dicarboxylic acid diester was liquid, it was isolated by distillation under reduced pressures, while if the resultant thiophene-2,5-dicarboxylic acid diester was solid, it was collected by filtration and recrystallized. The results are shown in the Table 5.

All the thiophene-2,5-dicarboxylic acid diesters obtained were found to have a gas chromatographic purity of more than 99.0%.

After the reaction, the reaction mixture was cooled to 60°-65° C., and there were added thereto 600 g of methanol, followed by stirring over a period of another hour at a refluxing temperature. Thereafter, the reaction mixture was cooled to room temperature, filtered and dried, to provide 404.8 g of 2,5-bis[5-tert-butylbenzoxazolyl-(2')]-thiophene as yellow crystals in a yield of 94.1%. Mp. 201°-202° C.

EXAMPLES 42-62

The reaction was carried out in the same manner as in the Example 41 using the thiophene-2,5-dicarboxylic acid diesters, aminophenols, acid catalysts and solvents as shown in the Table 6.

The results are shown in the Table 6, in which the compounds (A), (B) and (C) represent the compounds below, respectively.

Compound (A):

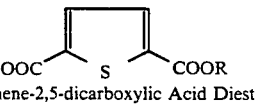

Thiophene-2,5-dicarboxylic Acid Diester

Compound (B):

TABLE 5

| Examples | Start Material R'OOC—S—COOR' (0.10 mole) | Solvent (100 ml) | Halogenating Agent (0.21 mole) | Additive (Alcohol) (mole) | Product R'OOC—S—COOR' | Yield (%) |
|---|---|---|---|---|---|---|
| 29 | R' = n-butyl | cyclohexane | Cl₂ | Cu (0.005) | R' = n-butyl | 96.0 |
| 30 | R' = methyl | chlorobenzene | Cl₂ | Cu (0.0010) | R' = methyl | 79.6 |
| 31 | R' = ethyl | cyclohexane | Cl₂ | Cu (0.0005) | R' = ethyl | 83.1 |
| 32 | R' = isopropyl | chlorobenzene | Cl₂ | CuCl (0.0005) | R' = isopropyl | 94.5 |
| 33 | R' = tert-butyl | n-hexane | Cl₂ | Fe (0.0050) | R' = tert-butyl | 81.9 |
| 34 | R' = isobutyl | 1,2,4-trichlorobenzene | Cl₂ | CuCl₂ (0.0010) | R' = isobutyl | 96.9 |
| 35 | R' = sec-butyl | n-hexane | Cl₂ | FeCl₂ (0.0100) | R' = sec-butyl | 97.1 |
| 36 | R' = n-octyl | cyclohexane | Cl₂ | FeCl₃ (0.0100) | R' = n-octyl | 93.1 |
| 37 | R' = phenyl | cyclohexane | Cl₂ | Zn (0.0020) | R' = phenyl | 93.2 |
| 38 | R' = m-tolyl | chlorobenzene | Cl₂ | ZnCl₂ (0.0010) | R' = m-tolyl | 92.9 |
| 39 | R' = benzyl | cyclohexane | SO₂Cl₂ | SnCl₂ (0.0030) | R' = benzyl | 92.8 |
| 40 | R' = n-butyl | n-hexane | Cl₂ | Cu (0.0005) | R' = n-butyl | 93.5 |

SYNTHESIS OF DIBENZOXAZOLYL THIOPHENES

EXAMPLE 41

In a 2 liter capacity four necked flask provided with a stirrer, a thermometer and a cooling tube were placed 284 g (1.0 mole) of thiophene-2,5-dicarboxylic acid di-tert-butyl ester, 330 g (2.0 mole) of 4-tert-butyl-2-aminophenol, 11.2 g of boric acid and 520 g of 1,2,4-trichlorobenzene under a nitrogen atmosphere, and the mixture was stirred at a temperature of 210°-220° C. over a period of four hours, while tert-butyl alcohol and water produced were removed by distillation.

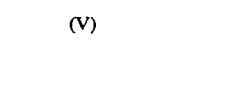

Aminophenols

Compound (C):

(V)

Dibenzoxazolyl Thiophenes
-continued

TABLE 6

| Examples | Compound (A) (1.0 mole) | Compound (B) (2.0 mole) | Acid Catalyst (0.18 mole) | Solvent (520 g) | Reaction Time (hr) | Compound (C) Mp. (°C.) | Yield (%) |
|---|---|---|---|---|---|---|---|
| 41 | R = tert-butyl | R' = tert-butyl | boric acid | 1,2,4-trichlorobenzene | 4 | R' = tert-butyl 201–202 | 94.1 |
| 42 | R = tert-butyl | R' = H | boric acid | 1,2,4-trichlorobenzene | 4 | R' = H 216–217 | 94.1 |
| 43 | R = tert-butyl | R' = 4-methyl | boric acid | 1,2,4-trichlorobenzene | 4 | R' = 5-methyl 215–216 | 93.8 |
| 44 | R = tert-butyl | R' = 3-methyl | boric acid | 1,2,4-trichlorobenzene | 4 | R' = 4-methyl 205–206 | 92.5 |
| 45 | R = tert-butyl | R' = 6-methyl | boric acid | 1,2,4-trichlorobenzene | 4 | R' = 7-methyl 213–214 | 93.3 |
| 46 | R = phenyl | R' = 4-tert-butyl | boric acid | 1,2,4-trichlorobenzene | 7 | R' = 5-tert-butyl 201–202 | 92.5 |
| 47 | R = phenyl | R' = 4-ethyl | $H_3PO_4$ | glycerine | 8 | R' = 5-ethyl 147–148 | 91.3 |
| 48 | R = phenyl | R' = 4-n-propyl | $ZnCl_2$ | glycerine | 8 | R' = 5-n-propyl 150–151 | 91.8 |
| 49 | R = phenyl | R' = isopropyl | $ZnCl_2$ | glycerine | 8 | R' = 5-isopropyl 142–143 | 90.5 |
| 50 | R = tert-amyl | R' = 4-sec-butyl | boric acid | diphenyl ether | 4 | R' = 5-sec-butyl 105–106 | 93.1 |
| 51 | R = tert-amyl | R' = 6-sec-butyl | boric acid | diphenyl ether | 4 | R' = 7-sec-butyl 233–234 | 92.8 |
| 52 | R = tert-amyl | R' = 4-cyclohexyl | boric acid | 1,2,4-trichlorobenzene | 4 | R' = 5-cyclohexyl 233–234 | 92.3 |
| 53 | R = m-tolyl | R' = 4-C(CH₃)₂—CH₂—C(CH₃)₃ | boric acid | 1,2,4-trichlorobenzene | 4 | R' = 5-C(CH₃)₂—CH₂—C(CH₃)₃ 200–201 | 90.5 |
| 54 | R = m-tolyl | R' = 5-phenyl | boric acid | diphenyl ether | 4 | R' = 6-phenyl 278–279 | 91.3 |
| 55 | R = m-tolyl | R' = 4-benzyl | boric acid | diphenyl ether | 4 | R' = 5-benzyl 199–200 | 90.0 |
| 56 | R = isopropyl | R' = 4-tert-butyl | boric acid | glycerine | 18 | R' = 5-tert-butyl 201–202 | 88.3 |
| 57 | R = isopropyl | R' = H | boric acid | 1,2,4-trichlorobenzene | 18 | R' = H 216–217 | 87.3 |
| 58 | R = sec-butyl | R' = H | boric acid | 1,2,4-trichlorobenzene | 18 | R' = H 216–217 | 87.9 |
| 59 | R = isobutyl | R' = H | boric acid | 1,2,4-trichlorobenzene | 18 | R' = H 216–217 | 88.5 |
| 60 | R = isobutyl | R' = 4-tert-butyl | boric acid | 1,2,4-trichlorobenzene | 18 | R' = 5-tert-butyl 201–202 | 89.1 |
| 61 | R = n-octyl | R' = 4-tert-butyl | boric acid | 1,2,4-trichlorobenzene | 18 | R' = 5-tert-butyl 201–202 | 85.5 |
| 62 | R = methyl* | R' = 4-tert-butyl | boric acid | 1,2,4-trichlorobenzene | 5 | R' = 5-tert-butyl 201–202 | 91.3 |

Note:
*The reaction was carried out at 240–250° C.

What is claimed is:

1. A method of producing a dibenzooxazolyl thiophene represented by the formula

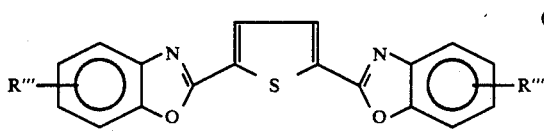
(V)

wherein R''' represents a hydrogen, an alkyl of 1–8 carbons, a cycloalkyl, a phenyl, a substituted phenyl or a benzyl, which comprises:

reacting a thiphene-2,5-dicarboxylic acid diester represented by the formula

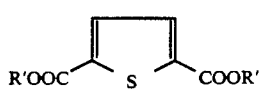
(I')

wherein R' represents a branched alkyl of 3–5 carbons, phenyl, or tolyl, with an aminophenol represented by the formula

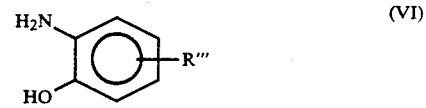
(VI)

wherein R''' is the same as before, in the presence of an acid catalyst, wherein the acid catalyst is boric acid, phosphoric acid, polyphosphoric acid, zinc chloride, ferric chloride, or sulfuric acid.

2. The method as claimed in claim 1 wherein the branched alkyl is isopropyl, isobutyl, sec-butyl, tert-butyl, isoamyl, sec-amyl or tert-amyl.

3. The method as claimed in claim 1 wherein R''' is hydrogen or tert-butyl.

4. The method as claimed in claim 1 wherein the acid catalyst is used in an amount of 0.05–0.5 moles per mole of the thiophene-2,5-dicarboxylic acid diester.

5. The method as claimed in claim 1 wherein the reaction is carried out at temperatures of 150°–220° C.

* * * * *